June 4, 1974 T. HEGG Plant Pat. 3,564
POINSETTIA PLANT
Filed Jan. 29, 1973
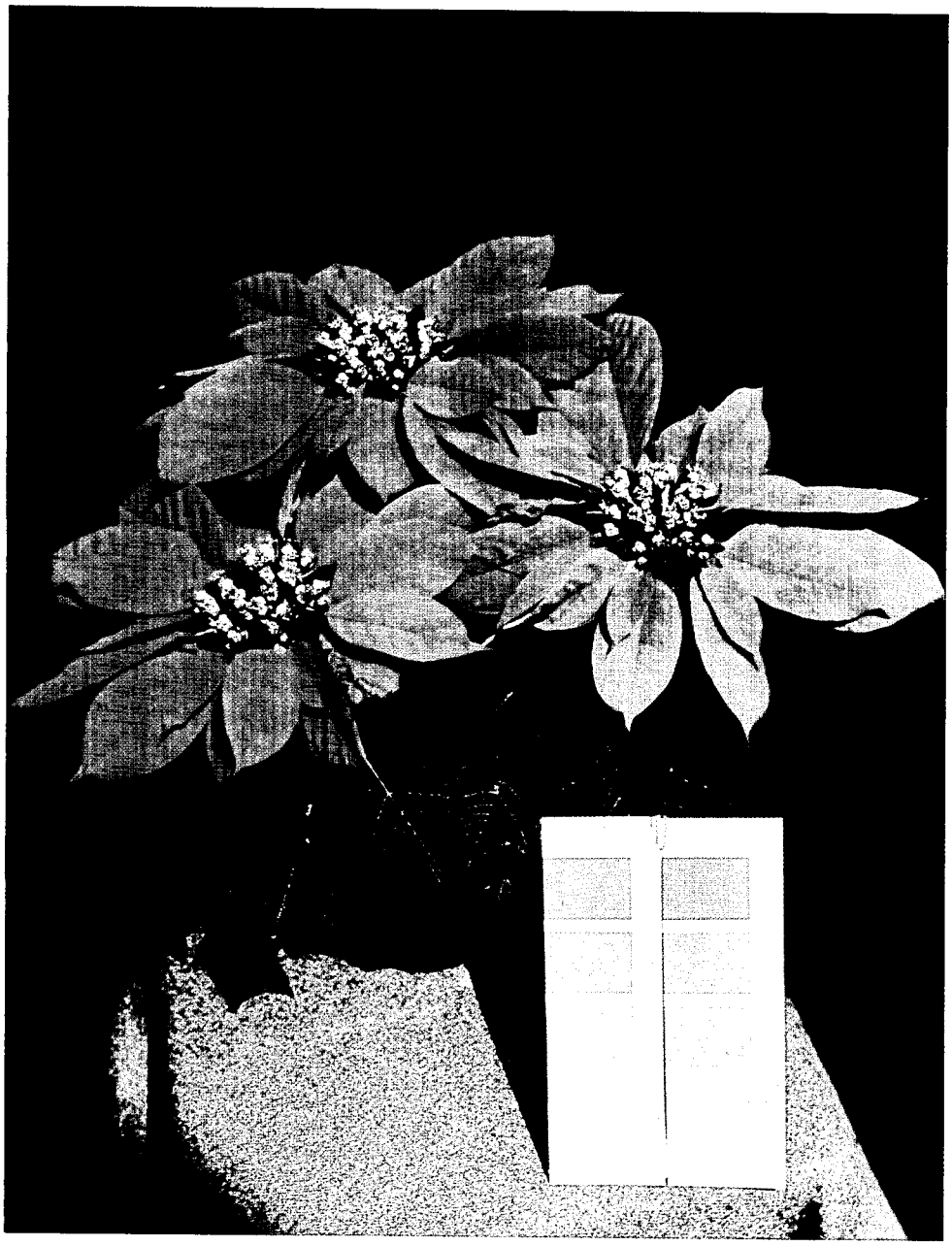

United States Patent Office

Plant Pat. 3,564
Patented June 4, 1974

3,564
POINSETTIA PLANT

Thormod Hegg, P.O. Box 66,
Reistad, Norway N-3425

Filed Jan. 29, 1973, Ser. No. 327,819
Int. Cl. A01h 5/00
U.S. Cl. Plt.—86 1 Claim The present invention relates to a new and distinct variety of poinsettia plant which was originated by me by crossing two unnamed and unpatented poinsettia varieties previously bred by me, but which have never been introduced in commerce.

At the time of this breeding, I was conducting in my nurseries at Lier, Norway, an extensive poinsettia breeding program in which I was seeking to produce and develop new and/or improved poinsettia varieties suitable for commercial production. The new variety which is the subject hereof is one of the outstanding seedlings which resulted from this program. It constitutes a new and improved variety as evidenced by the following unique combination of particularly outstanding characteristics which distinguish the same from its parents, as well as from all other poinsettia varieties of which I am aware:

(1) A semi-dwarf, self-branching and strong habit of growth, with short internodes, which makes the plant very attractive for pot plant production;
(2) Strong, thick, stiff and free-branching stems on which the bracts and flowers can be easily shaped to make a well-proportioned plant;
(3) Distinctive and attractive, shiny dark green leaves which are rough textured and leathery in appearance on their upper surfaces, with the leaves being prominently veined and more strongly lobed than those of other varieties;
(4) A distinctive and attractive deep orange-red bract color;
(5) A long-lasting plant habit; and
(6) An ability to be easily brought into flower at any time of the year by subjecting the same to short day treatment.

Asexual reproduction of my new poinsettia variety in my nurseries located at Lier, Norway, as performed by me by vegetative cuttings, shows that the foregoing characteristics and distinctions come true and are established and transmitted through succeeding propagations.

The accompanying drawing shows a typical specimen plant of my new poinsettia variety as depicted in color in comparison with appropriate color scales applicable particularly to the bract and foliage colors.

The following is a detailed description of my new variety, with color terminology in accordance with The Royal Horticultural Society Colour Chart from which the illustrated color scales were selected, except where general color terms of ordinary dictionary significance are obvious:

Locality where grown and observed: Lier, Norway.
Breeding: Selected seedling derived from crossing two unnamed and non-commercial varieties selected from my private breeding stock plants.
Propagation: Holds its distinguishing characteristics through succeeding propagations by vegetative cuttings.

Form: Medium height or semi-dwarf (when not treated with growth retardants).
Habit of growth: Strong, self-branching average growth; when pinched, branches grow upright and plant becomes well-proportioned; branches freely, with uniform shoots carrying the bracts at almost the same height and presenting an attractive form for pot plant production; side shoots developing on stems produce both new bracts and flowers, not only vegetative shoots, contrary to other known varieties.
Rooting habit: Roots easily, and new roots develop relatively fast in a short time.
Blooming habit: Early; requires fewer short days to form flowers than most other known varieties; with short day treatment, can be brought into flower in 9 to 10 weeks.
Blooming season: Can be brought into bloom at any time of the year, and easily predictable for Christmas season blooms.
Foliage:
*Shape.*—Very strongly lobed (more than in other varieties which have leaves of generally similar characteristics).
*Texture.*—Rough upper surface, giving leathery appearance.
*Veins.*—Prominent.
*Color.*—Shiny dark green (somewhat darker than Green Group–A), giving the plant a very healthy appearance.
Bracts: Normal number.
*Shape.*—Oval, with pointed tips.
*Color.*—Deep orange-red, near Red Group 42–A.
Flowers: Grouped closely together; long-lasting.
Reproductive organs:
*Stamens.*—Borne in dense clusters. Color—Yellow.
*Nectar cups.*—Well developed. Color—Deep yellow. Ovaries—Present.
Disease resistance: Under normal conditions, is not readily subject to soil borne diseases common to poinsettia varieties, as determined by comparison with other varieties grown under the same conditions at Lier, Norway.

I claim:

1. A new and distinct variety of poinsettia plant, substantially as herein shown and described, characterized particularly as to novelty by the unique combination of a semi-dwarf, self-branching and strong habit of growth, with short internodes, which makes the plant very attractive for pot plant production, strong, thick, stiff and free-branching stems on which the bracts and flowers can be easily shaped to make a well-proportioned plant, distinctive and attractive shiny dark green leaves, which are rough textured and leathery in appearance on their upper surfaces, with the leaves being prominently veined and more strong lobed than those of other varieties, a distinctive and attractive deep orange-red bract color, a long-lasting plant habit, and an ability to be easily brought into flower at any time of the year by subjecting the same to short day treatment.

No references cited.

ROBERT E. BAGWILL, Primary Examiner